US 6,599,299 B2
Jul. 29, 2003

(12) United States Patent
Schultz

(10) Patent No.: US 6,599,299 B2
(45) Date of Patent: Jul. 29, 2003

(54) DEVICE AND METHOD FOR BODY LUMEN OCCLUSION

(76) Inventor: Leonard S. Schultz, 11036 Boone Cir. South, Bloomington, MN (US) 55138

(*) Notice: Subject to any disclaimer, the term of this patent is extended or adjusted under 35 U.S.C. 154(b) by 0 days.

(21) Appl. No.: 09/891,961

(22) Filed: Jun. 26, 2001

(65) Prior Publication Data

US 2002/0198547 A1 Dec. 26, 2002

(51) Int. Cl.$^7$ ............................................. A61B 17/12
(52) U.S. Cl. ........................................ 606/151; 606/195
(58) Field of Search ................................ 606/157, 170, 606/151, 195, 108, 198, 312, 158; 604/907

(56) References Cited

U.S. PATENT DOCUMENTS

| | | | | |
|---|---|---|---|---|
| 3,834,394 A | * | 9/1974 | Hunter et al. | 604/907 |
| 4,085,757 A | * | 4/1978 | Pevsner | 604/907 |
| 4,263,917 A | * | 4/1981 | Moss | 600/433 |
| 4,781,677 A | | 11/1988 | Wilcox | 604/28 |
| 5,071,419 A | | 12/1991 | Rydell et al. | 606/48 |
| 5,159,925 A | | 11/1992 | Neuwirth et al. | 128/401 |
| 5,167,614 A | * | 12/1992 | Tessmann et al. | 604/8 |
| 5,171,311 A | | 12/1992 | Rydell et al. | 606/48 |
| 5,201,746 A | | 4/1993 | Schichman | 606/151 |
| 5,334,210 A | * | 8/1994 | Gianturco | 604/907 |
| 5,443,449 A | | 8/1995 | Buelna | 604/405 |
| 5,643,254 A | | 7/1997 | Scheldrup et al. | 606/32 |
| 5,709,224 A | | 1/1998 | Behl et al. | 128/898 |
| 5,743,905 A | | 4/1998 | Eder et al. | 606/32 |
| 5,776,126 A | | 7/1998 | Wilk et al. | 606/1 |
| 5,817,046 A | | 10/1998 | Glickman | 604/5.04 |
| 5,860,426 A | | 1/1999 | Kleiman | 128/898 |
| 6,019,757 A | | 2/2000 | Scheldrup | 606/49 |
| 6,077,261 A | | 6/2000 | Behl et al. | 606/50 |
| 6,241,762 B1 | | 6/2001 | Shanley | 623/1.17 |
| 6,245,101 B1 | | 6/2001 | Drasler et al. | 623/1.15 |
| 6,246,914 B1 | | 6/2001 | de la Rama et al. | 607/122 |

OTHER PUBLICATIONS

J.R. Coll. Surg. Edinb., 42, Dec. 1997, 389–394 Evolving management of common bile duct stones in the laparoscopic era Fanning, N.F., et al.
J. R. Coll. Surg. Edinb., 44, Jun. 1999, 200–2 Migration of three endoclips following laparoscopic cholecystectomy, Kong, C. K., et al.
Gallstones and Laparoscopic Cholecystectomy, NIH Consens Statement Online Sep. 14–16, 1992; 10(3):1–20.
http://www.limit.ac.uk/lapchole1.htm.
http://www.limit.ac.uk/lapchole2.htm.
http://www.limit.ac.uk/lapchole3.htm.
http://userpages.umbc.edu/~mccormac/acc.htm.
Harrison's Principles of Internal Medicine, Twelfth Edition, McGraw–Hill, Inc., New York, N.Y., pp. 1358–1368 (1991).
Surg Today 1997;27(10):907–9 Acute acalculous cholecystitis after cardiovascular surgery. Saito, A., et al.
J Cardiovasc Surg 1997;38:513–5 Percutaneous transhepatoc gallbladder drainage for acute acalculous cholecystitis following cardiovascular surgery. Ishikawa, S., et al.
J Cardiovasc Surg 1998;39:95–7 Management of postoperative fever in cardiovascular surgery. Ishikawa, S., et al.
Eur J Ultrasound 1999 Jul.;9(3):207–12 Application of trocar technique in ultrasound–guided drainage of the gallbladder. Federmann, G., et al.

(List continued on next page.)

*Primary Examiner*—Danny Worrell
(74) *Attorney, Agent, or Firm*—Dorsey & Whitney LLP

(57) ABSTRACT

The present invention provides a device and method for occluding the body lumen including the cystic duct, wherein, in one embodiment, the device has a tapered end and an expandable segment. In use, using a suitable access instrument, the tapered end of the device is inserted into the cystic duct and the expandable segment may be expanded to lodge the device in the duct and to occlude the duct. The access instrument may then be detached from the device and withdrawn. The device is left in the duct, acting as a plug.

8 Claims, 5 Drawing Sheets

OTHER PUBLICATIONS

Br. J. Surg. 1993, vol. 80, Nov., 1440–1442 Percutaneous transhepatic cholecystostomy for acute acalculous cholecystitis. Shirai, Y., et al.

JSLS (2001) Apr.–Jun.;5(2):183–5 Acalculous Cholecystitis in a Two Year Old. Croteau, D., et al.

Am Surg 1993 Feb.;59(2):74–7 Acute acalculous cholecystitis following open heart surgery. Sessions, S., et al.

J. Clinical Laser Medicine & Surgery 11.3 (1993):135–137 Laparolithic Cholecystectomy: Laboratory Data and First Clinical Case. Schultz, L., et al.

* cited by examiner

DEVICE AND METHOD FOR BODY LUMEN OCCLUSION

BACKGROUND

This invention relates to medical devices, methods for making them, and methods for their use. More particularly, the present invention relates to the methods and devices for occluding body lumens by delivering a plugging means into a lumen with or through a detachable access catheter. In one exemplary use, The invention may be used to occlude the cystic duct for preventing bile leakage in the field of treating gallstone and gallbladder disease.

Bile is first produced in the liver, then secreted into a complex network of ducts, and eventually enters into the hepatic duct. The bile then passes through the cystic duct and enters into the gallbladder. The cystic duct is at the narrow end of the gallbladder. It is the passage by which the contents of the gallbladder drain into another slightly larger tube called the common bile duct. The gallbladder concentrates and stores bile. When food enters the small intestine, a hormone called cholecystokinin is released, signaling the gallbladder to contract. The contraction of the gallbladder propels the bile back through the cystic duct and into the common bile duct, which leads bile into the duodenum. The bile then emulsifies fatty molecules so that fat and the fat-soluble vitamins A, D, E, and K can be absorbed through the intestinal lining. A sphincter is present at the duct-duodenum juncture.

Bile is composed of water, bile salts, lecithin and cholesterol. Cholesterol makes up only $\frac{1}{20}$ of bile. It is not very soluble and must be properly balanced with bile salts to remain suspended in fluid. If the liver secretes too much cholesterol into the bile, cholesterol may then precipitate out of the bile solution to form gallstones, a condition known as cholelithiasis.

Gallstones are quite prevalent in most western countries. Cholelithiasis incidence increases with age. In the United States, at least $\frac{1}{5}$ of women, and $\frac{2}{25}$ of men over the age of 40 are affected by gallstones. More than 20 million people in the U.S. have gallstones, and approximately 1 million new cases of cholelithiasis develop every year.

Gallstones usually produce noticeable symptoms by causing inflammation, narrowing (stenosis) or obstruction of the cystic duct, common bile duct or sphincter following their exit from the gallbladder. Although there has been some success with drug- or shockwave-mediated dissolution of gallstones, the current therapy of choice is surgery, either by excision of the gallbladder (cholecystectomy) or draining the gallbladder with a tube (cholecystostomy). *Harrison's Principles of Internal Medicine*, Twelfth Edition, McGraw-Hill, Inc., New York, N.Y., pp. 1358–1368 (1991). In 1991 approximately 600,000 patients underwent cholecystectomy. Gallstones and Laparoscopic Cholecystectomy, NIH Consens Statement Online Sep. 14–16, 1992, 10(3):1–20. Jun. 25, 2001 <http://odp.od.nih.gov/consensus/cons/090/090_statement.htm>.

Traditionally, there are two ways to perform a cholecystectomy: an open cholecystectomy and a laparoscopic cholecystectomy. In an open cholecystectomy, the surgeon removes the gallbladder through a 2 to 4 inch incision in the patient's abdomen. In a laparoscopic cholecystectomy, the surgeon inserts a laparoscope into the patient's body through a tiny cut (¼"–b ½") made just below the patient's navel. A laparoscope is a long, slender optical instrument that has lenses and a powerful light. The laparoscope is attached to a television camera and allows the surgeon to see the patient's gallbladder on a television screen and do the surgery with tools inserted in three other small cuts made in the right upper part of the patient's abdomen. The surgeon removes the gallbladder through one of the incisions. The advantages of laparoscopic cholecystectomy over open cholecystectomy are shorter postoperative recovery time, less pain and better cosmetic results.

The technical problems of dissecting the gallbladder from the liver include stone spillage with puncture site infection, liver bed bleeding, and difficult removal of the stone laden gallbladder through a 1-cm incision. These potential problems can be eliminated by a new method which combines lithotriptic emulsification (mechanical liquification) of gallstones with removal of the free gallbladder wall and ablation of the remaining gallbladder mucosa. Schultz, L. S., Cartmill, J. A., Graber, J. N., Hickok, D. F. "Laparolithic cholecystectomy: Laboratory data and first clinical case." *J. Clinical Laser Medicine & Surgery* 11.3 (1993): 135–137.

Whichever the technique is used, the surgeon must dissect the cystic artery and duct and occlude them with metal clips or ligature before removal of the gallbladder. The cystic duct clip or ligature prevents spillage of bile from the gallbladder and its leakage from the liver. Bile leakage from the cystic duct is one of the most common problems following the cholecystectomy. The leakage could be due to incomplete duct occlusion or dislodgement of a loosely placed clip or ligature from the cystic duct stump. Further, the clip may migrate into the common bile duct, where it can induce cholesterol stones, resulting in severe abdominal and back pain. Experts in the field recommend that surgeons exercise great care to ensure secure occlusion of the cystic duct during the cholecystectomy. At the present time, occlusion of the cystic duct is to be considered permanent although future research may indicate benefits from temporary occlusion.

Occlusion of the cystic duct can also be a helpful adjunct in combination with percutaneous transhepatic catheter lithotripsy and cholecystostomy for treatment of acute acalculous cholecystitis as may be seen following cardiac bypass surgery. Acute acalculous cholecystitis is inflammation of the gallbladder without calculi. In the study period 1982–1990, 0.34% of the patients following open heart surgery developed acute acalculous cholecystitis. Some causes of acute acalculous cholecystitis include hypoperfusion of the gallbladder due to cardiovascular bypass surgery, visceral atherosclerosis, or low cardiac output.

Although the management of acute acalculous cholecystitis following heart surgery remains controversial, percutaneous transhepatic gallbladder drainage is found to be a safe and effective procedure. Ishikawa, S., Ohtaki, A., Koyano T., Takahashi T., Sato, Y., Nakamura, S., Ohwada, S., Morishita, Y.; "Percutaneous transhepatic gallbladder drainage for acute acalculous cholecystitis following cardiovascular surgery." *J. Cardiovasc. Surg.* 38.5 (1997): 513–5. The drainage (cholecystostomy) is for temporary management (to get over infection), and at the present time, cystic duct occlusion is permanent and should be part of gallbladder removal or, in this case, defunctionalization. In such cases, catheter-guided occlusion of the cystic duct would be an useful, adjunctive therapy in conjunction with chemical or mechanical ablation of the mucosa to defunctionalize the gallbladder.

There is a need in the art for an alternative method and device of occlusion of body lumens. There is a further need for a method and device of secure occlusion of the cystic duct to prevent bile spillage during and after non-surgical methods of defunctionalization of the gallbladder as an alternative to open or laparoscopic surgery.

SUMMARY

This invention provides devices and methods for occluding a body lumen. According to one embodiment of the invention, the lumen occluding device comprises means for plugging the body lumen and means for fixing the means for plugging in place.

In one embodiment, the means for plugging comprises a tapered segment, and the means for fixing comprises an expandable segment which is generally adjacent to the tapered segment. In another embodiment, the expandable segment further includes structures suitable for attaching the expandable segment to the interior wall of the lumen. In some embodiments, the structures for attaching the means for plugging to the interior wall of the lumen have a shape like tooth, or hook, or the like. In other embodiments, the means for fixing comprises a segment having numerous openings of suitable sizes, shapes, and spaces between them.

In some embodiments, the occlusion device of the present invention comprises a delivery instrument detachably coupled to the means for plugging. In one embodiment, the delivery instrument comprises an access catheter separably coupled to the means for plugging, and a maneuverable catheter core flexibly placed inside the catheter.

In one embodiment of the method of the present invention, using a suitable delivery instrument, the means for plugging is inserted into a target lumen, moved to a selected location, and then fixed to the interior wall of the lumen. The delivery instrument is then detached from the means for plugging and withdrawn from the lumen, leaving the means for plugging in the selected location as an occluding device. While at the present time, and as concerns occlusion of the cystic duct, the present assertion may be used to permanently plug or occlude a body lumen, the present invention is intended to encompass semi-permanent or temporary plugging or occlusion of body lumens.

In some embodiments of the method, the lumen occluding device is inserted into the body lumen, such as the cystic duct, through an incision in an abdominal wall of a human patient. In another embodiment of the method, the occluding device may be inserted into the fallopian tubes for plugging or occlusion providing for contraception.

In another embodiment of the method of the present invention, the means for plugging is advanced to the selected location of a body lumen, then a portion of it is expanded against the interior wall of the lumen and thereby occludes the lumen. The delivery instrument is then detached and removed from the body lumen.

In another embodiment of the method, a means for plugging with numerous openings is inserted into a selected location of a body lumen, then a biological bonding agent is injected into its delivery instrument. After delivery to the occluding device, the biological bonding agent is extruded through the openings and binds the means for plugging to the interior wall of the lumen. The delivery instrument is then detached and withdrawn from the lumen.

The illustrative embodiments presented herein demonstrate the present invention. Other embodiments and variations based on the embodiments, concepts and principles set forth herein are within the scope of the invention. Additional embodiments, features and advantages of the present invention may be appreciated by reference to the following description and to the appended drawings and claims.

DETAILED DESCRIPTION

Figure 1A:
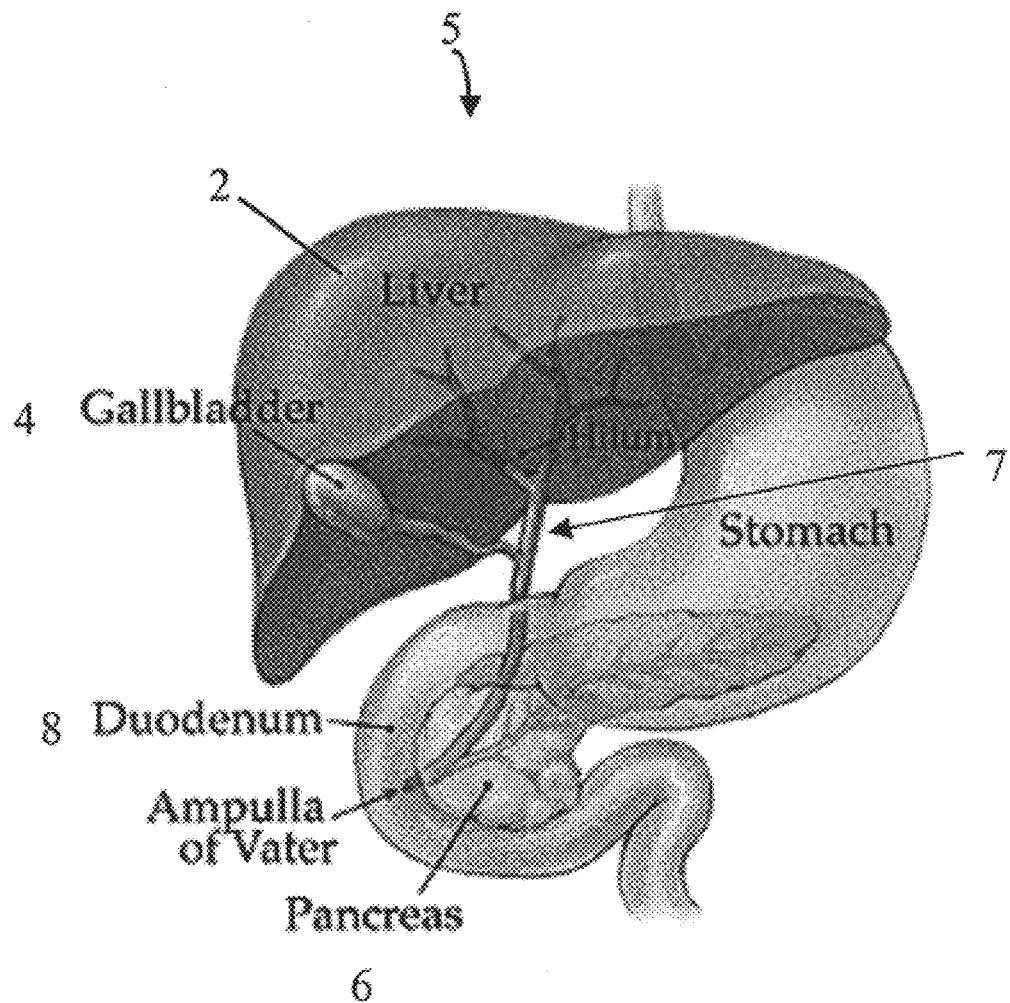
FIGS. 1A and 1B show an exemplary system in which the present invention may be used.

The accompanying figures and this description depict and describe embodiments of a medical device in accordance with the present invention, and features and components thereof. The present invention also encompasses a method of making and using embodiments of the medical device. As used herein, the term "medical" is intended to have its common, dictionary meaning, namely: of, relating to, or concerned with physicians or the practice of medicine, including veterinary medicine. Thus, the term "medical device" is intended to encompass instruments, tools, implants, therapeutic structures and mechanisms, prosthetics and the like, and methods of their use and manufacture, relating to the practice of medicine or medical treatment. The terms plug or occlude (and plugging or occluding) are intended to have their dictionary meaning.

With regard to fastening, mounting, attaching or connecting components of the present invention to form the medical device as a whole, unless specifically described otherwise, such are intended to encompass conventional fasteners such as threaded or bayonet connectors, snap rings, detent arrangements, clamps, rivets, toggles, pins and the like. Components may also be connected by adhesives, glues, welding, ultrasonic welding, or friction fitting or deformation, if appropriate, and appropriate liquid and/or airtight seals or sealing devices may be used. Electronic portions of the device, if any, or associated electrical devices (such as sensors, associated delivery, treatment or visualization equipment, etc.) may use conventional, commercially available electronic components, connectors and devices such as suitable wiring, connectors, printed circuit boards, microchips, transmitters or signal emitters and/or receivers, lights, LED's, liquid crystal displays, pressure sensors, liquid sensors, audio components, inputs, outputs and the like. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, pressing, extruding, molding and machining may be used.

Any references to front and back, right and left, top and bottom and upper and lower are intended for convenience of description, not to limit the present invention or its components to any one positional or spatial orientation.

The methods and devices of the present invention will be useful for selectively occluding virtually any body lumen, of a human or animal body, having a luminal wall that can be mechanically closed followed by delivery of plugging means. As used herein, "lumen" is defined as the space or cavity in the interior of a tubular structure or organ, such as an artery, vein, tube or duct, such as the bile duct. While the present invention will find one use in occluding or plugging the cystic duct, it will also find use with other body lumens, such as blood vessels, the fallopian tubes, and ureter, etc. In some embodiments, the present invention may be adapted for temporary occlusion of body lumens.

Figure 1B:
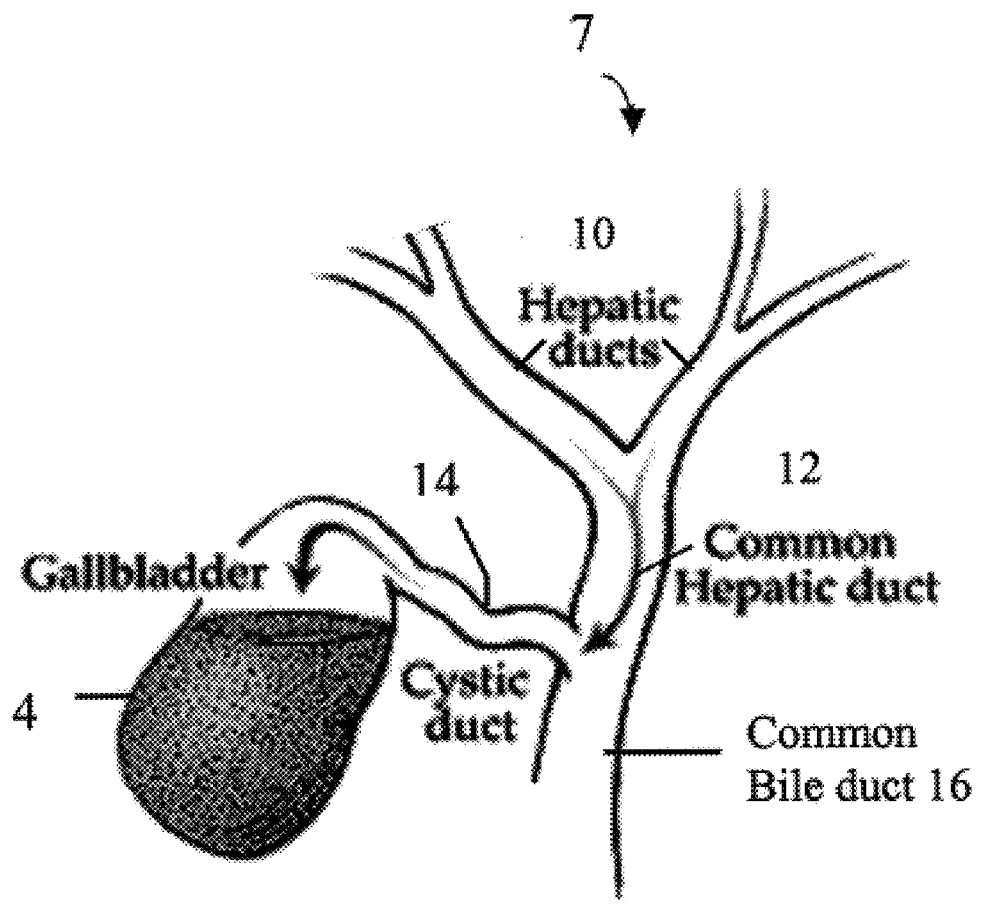

FIG. 1A shows an exemplary system 5 in which the present invention may be used. As shown in FIG. 1A, the tubular system 7 connects the liver 2, gallbladder 4, pancreas 6 and duodenum 8. FIG. 1B shows a part of the tubular system 7, including the hepatic ducts 10, common hepatic duct 12, cystic duct 14 and common bile duct 16.

Figure 2:
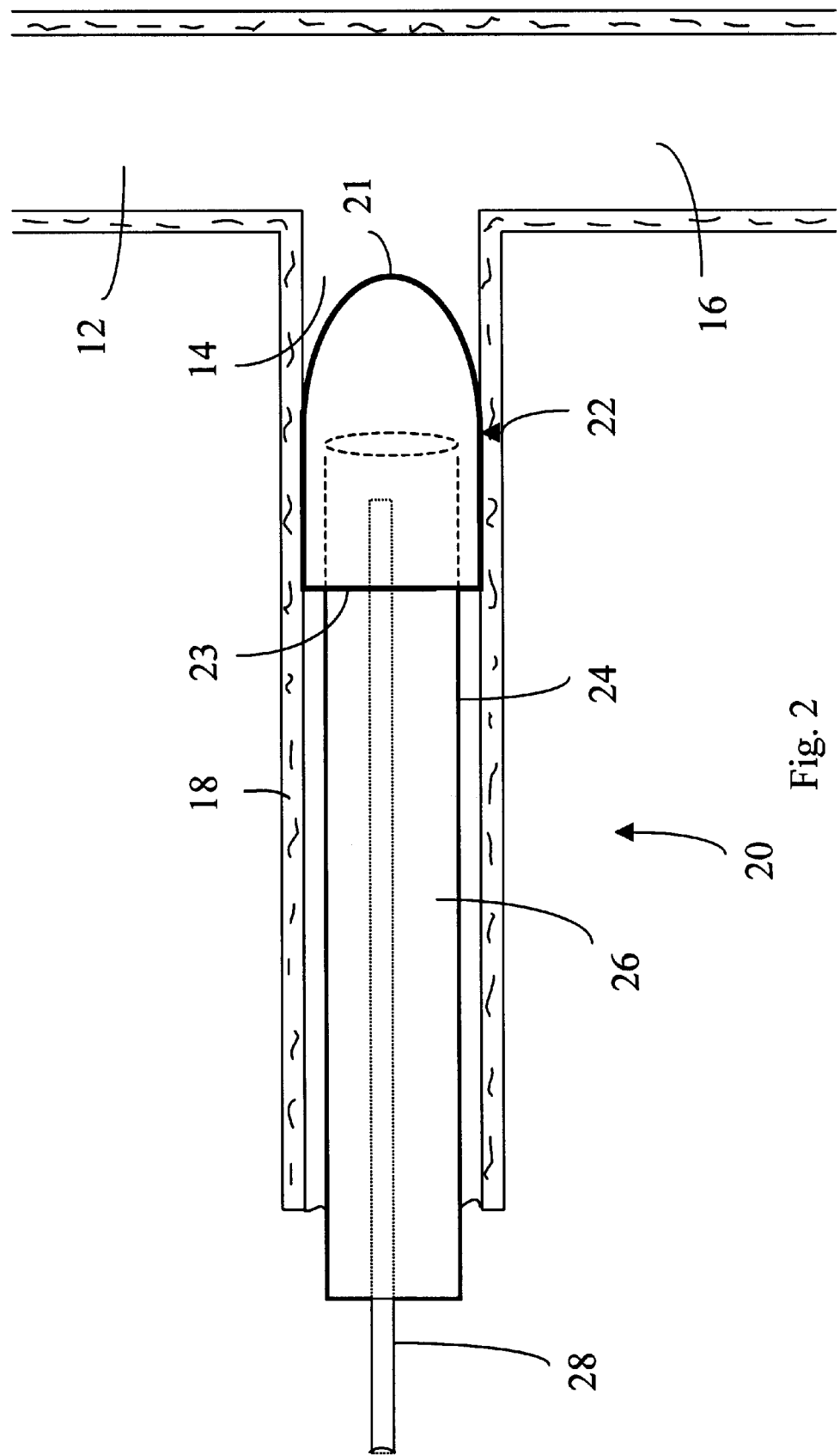
FIG. 2 shows one embodiment of the present invention for use in occluding a cystic duct.
Figure 3:
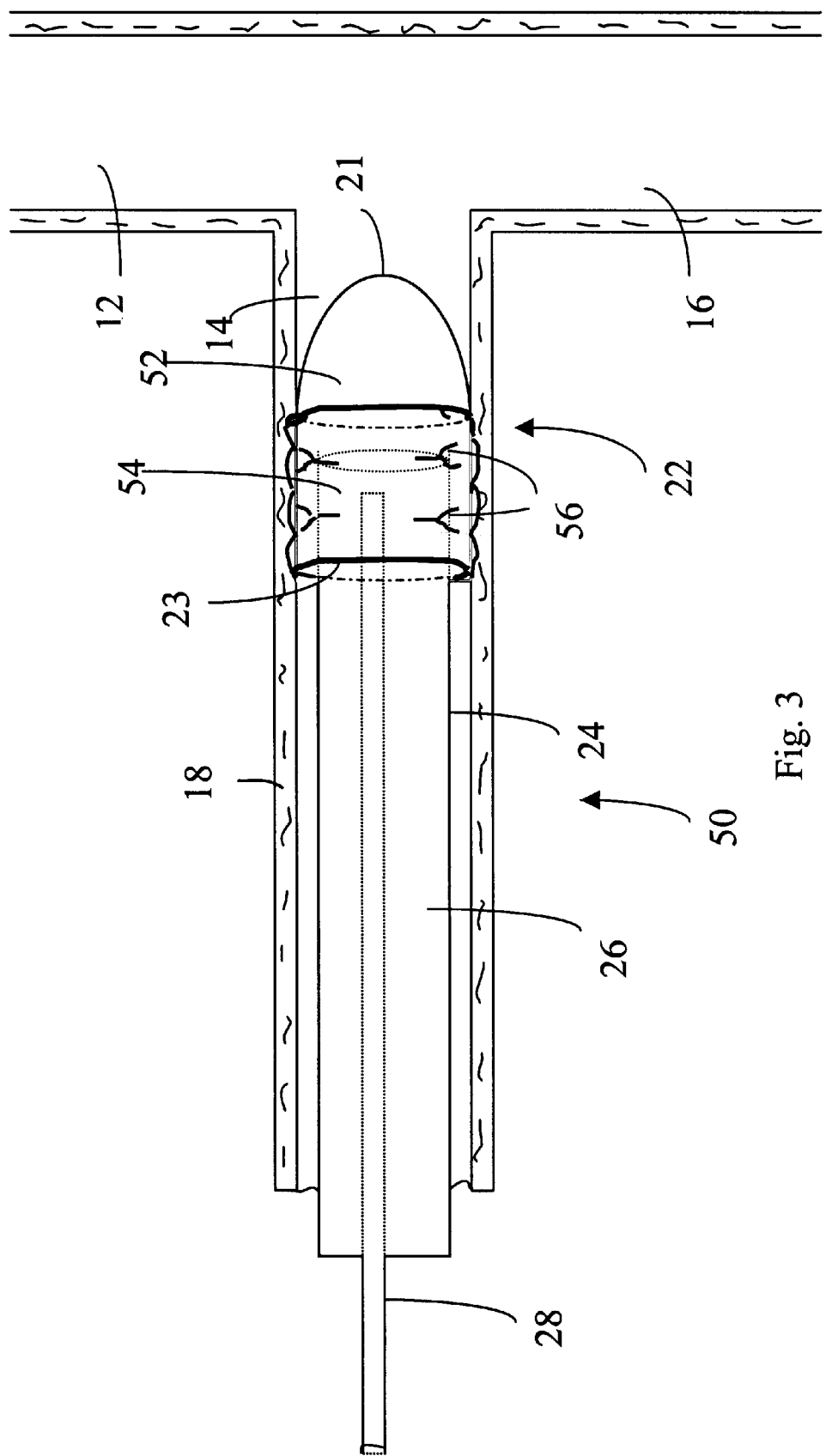
FIG. 3 shows another embodiment of the present invention for use in occluding a cystic duct.
Figure 4:
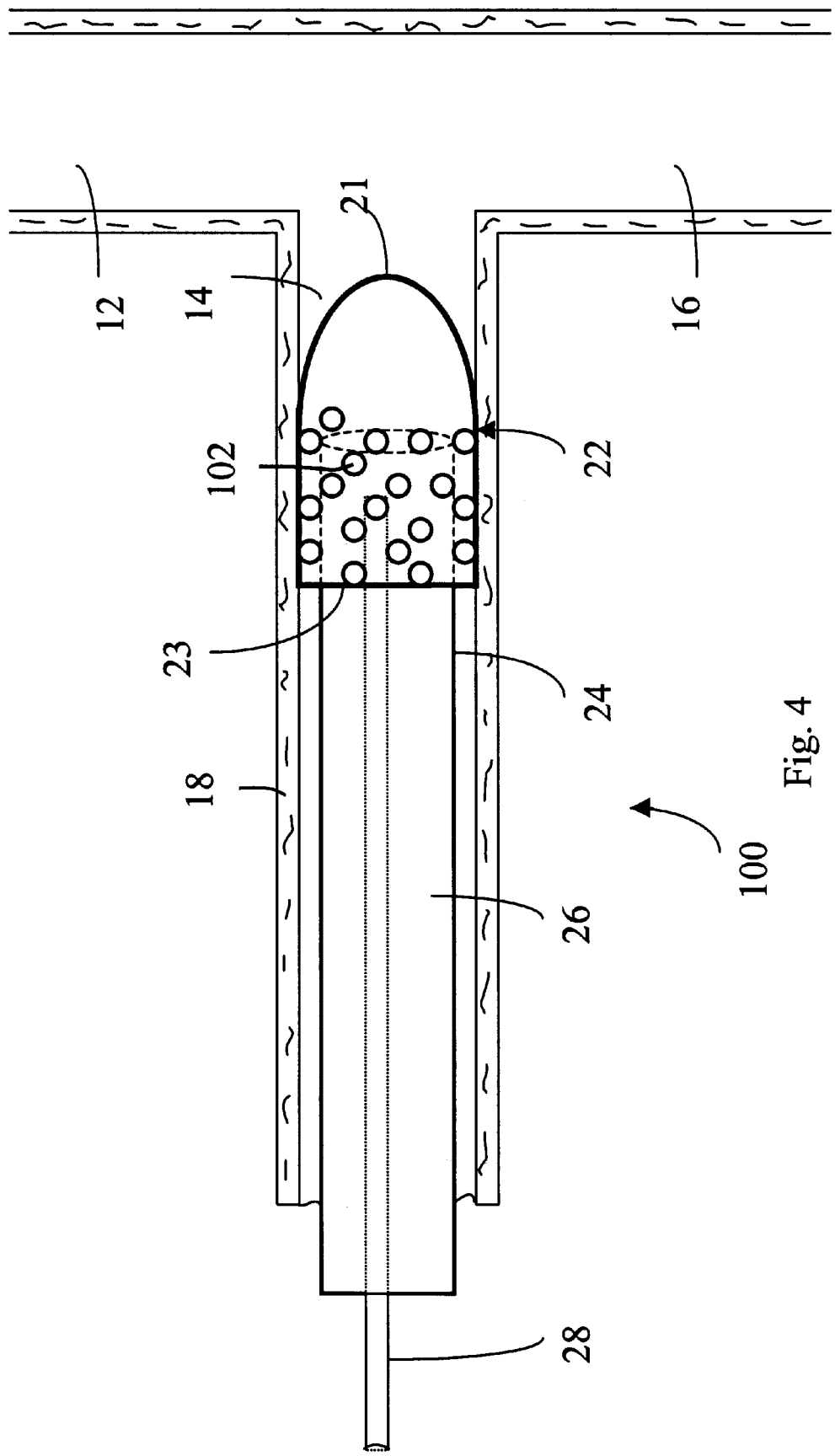
FIG. 4 shows another embodiment of the present invention for use in occluding a cystic duct.

The drawings in FIGS. 2–4 illustrate embodiments of the occlusion device and its use. Like numerals indicate like elements. FIG. 2 shows the occlusion device 20 constructed according to the principles of the present invention, comprising a generally cylindrical body for forming a plugging means 22, and a delivery means 24 operably and releaseably coupled to the plugging means 22. One end 23 of the plugging means is generally circular and may be closed or open, the other end 21 is tapered, and the degree of taper may be varied as long as it facilitates the introduction of the device into a duct or the like without injuring tissue. The plugging means 22 may be partially or completely solid.

Although in one embodiment, the delivery means 24 is detachably coupled to the tapered plugging means 22, other arrangements may be possible. For example, the occlusion device 20 may have a coupling structure (not shown) permanently connected to the plugging means 22, and the delivery means 24 may be detachably connected to the coupling structure.

The size of the tapered plugging means 22 will be suitable for insertion and occlusion of the intended site. It typically has a length in the range from 1 cm to 2 cm. Most of the lumens of the body, including the cystic duct 14, can be gently dilated. In some embodiments, the width or diameter of the tapered plugging means will therefore be slightly greater than the internal diameter of the lumen intended for occlusion, usually in the range from 1 mm to 5 mm, whereby friction may make it more easily controllable and help hold it in place, at least temporarily. Whatever diameter is selected, the plugging means 22 should substantially occupy, close or plug the lumen of the duct or tube in which it is being used.

Any suitable delivery device or method may be used to deliver the plugging means 22 to the selected location. For example, the delivery means 24 may be in the form of a conventional catheter body, typically having a length in the range from 40 cm to 200 cm, usually from 70 cm to 125 cm. The catheter body will have an outside diameter consistent with its intended use, typically being from 1 mm to 5 mm, usually from 2 mm to 4 mm.

FIG. 2 shows one embodiment of the delivery means 24 that comprises an access catheter 26 and a maneuverable catheter core 28. The maneuverable core 28 is flexibly placed inside the access catheter 26 for guiding the delivery of the tapered plugging means 22 to a selected site in the body lumen of a patient.

To occlude the cystic duct 14, the operator will insert the occlusion device 20 with the plugging means 22, particularly the tapered end 21, entering the duct first. With the aid of the maneuverable core 28, the operator will deliver the plugging means 22 to a selected site, for example, a site near the junction of the cystic duct 14, common hepatic duct 12 and common bile duct 16. The operator will then fix the plugging means 22 onto the interior wall 18, and detach and withdraw the delivery means 24, leaving the plugging means 22 lodged inside the cystic duct 14.

FIG. 3 shows another embodiment of the occlusion device 50 of the present invention, wherein the plugging means 22 comprises a tapered segment 52 and an immediately adjacent, expandable segment 54. The tapered segment 52 and the expandable segment 54 may be an integral, one-piece body, or may be two parts which are permanently connected to each other. In one embodiment, the expandable segment 54 is generally cylindrical, having generally the same diameter as the non-tapered portion 23 of the plugging means 22, and is expandable generally radially from the central longitudinal axis of the device 50 so that, when the device 50 is positioned at the selected location in the lumen, the expandable segment may be expanded to form a tight-fitting plug.

In another embodiment, the expandable segment 54 comprises a plurality of structures 56 for attaching the expandable segment 54 to the interior wall 18 of the cystic duct 14 or other lumen. The structures 56 may be of any desired shape and size and there may be any selected number of structures 56, as long as a suitable connection may be formed between the structures 56 and the wall 18. For example, in one embodiment, the structures 56 for attaching the expandable segment 54 to the interior wall 18 of the lumen 14 have a shape like a tooth or a hook. In some embodiments, the structures 56 may comprise the expandable feature of the expandable segment 54. That is, the structures 56 may be moved outwardly relative to the outermost surface of the expandable segment 54 so the outmost surface of the expandable segment 54 becomes irregular rather than smooth.

FIG. 4 shows another embodiment of the occlusion device 100 in which the plugging means 22 further comprises a plurality of openings 102. These openings 102 may be evenly or unevenly spaced from each other, and their shapes may be round, oval or any other shape suitable for allowing the passage or flow-through of a biological bonding agent. To occlude the cystic duct 14 or other body lumen, the operator will inject a biological bonding agent such as a surgical glue or tissue bonding or binding agent into the access catheter 26. After sliding down to the plugging means 22, the surgical glue or tissue bonding or binding agent will extend or extrude through the openings 102, and bind the plugging means 22 to the interior wall 18 of the cystic duct 14. The operator then detach and withdraw the access catheter 26.

One exemplary method of making the occlusion device 50 of the present invention comprises forming the plugging means 22 using suitable forming or manufacturing methods adapted to the material of which the plugging means 22 is made; forming the expandable segment 54 using suitable forming or manufacturing methods adapted to the material of which the expandable segment 54 is made; and connecting the plugging means 22 and the expandable segment 54 using suitable, connecting methods.

Both the plugging means 22 and the delivery means 24 may be manufactured from a variety of conventional materials, including natural and synthetic polymers, such as polyvinyl chloride, polyurethanes (PTFE's), nylons, and the like. They may be optionally reinforced to enhance their strength, flexibility, and the like. Exemplary reinforcement layers include metal fiber braids, polymeric fiber braids, meal or fiber helical windings, and the like. Optionally, a portion of the access catheter could be formed from a metal rod or hypo tube.

The expandable segment may be manufactured from a variety of inflatable materials such as silicone, latex, polyurethane, thermoplastic elastomer, polyethylene balloon, cross-linked polyethylene balloon, polyethylene terephthalate balloon, and the like.

Although the present invention has been described with reference to embodiments, persons skilled in the art will recognize that changes may be made in form and detail without departing from the spirit and scope of the invention. The described embodiments should be considered in all respects as illustrative, not restrictive, and reference should be made to the appended claims for determining the scope of the invention.

I claim:

1. A method of occluding a body lumen, the method comprising:

providing a device comprising a plugging means adapted for occluding the body lumen and a delivery means, wherein the plugging means has a plurality of openings and the delivery means is detachably coupled to the plugging means;

inserting said device into the body lumen with the plugging means entering the lumen first;

advancing said device through said body lumen to a target site;

injecting a biological bonding agent into the delivery means;

sliding the bonding agent down to the plugging means;

extruding said bonding agent through the openings of said plugging means;

binding said plugging means onto interior wall of said body lumen;

detaching the delivery means from said plugging means; and withdrawing said delivery means from said body lumen, leaving said plugging means inside said body lumen.

2. The method of claim 1, wherein the delivery means comprises an access catheter detachably coupled to the means, and a maneuverable core flexibly placed inside the access catheter.

3. The method of claim 1 wherein said body lumen is a cystic duct.

4. The method of claim 1 wherein said body lumen is fallopian tubes.

5. The method of claim 1, wherein the step of inserting said device is through an incision in an abdominal wall of a human patient.

6. A lumen occlusion device, said device comprising:

means for plugging the lumen;

means for fixing means for plugging to interior wall of the lumen; and delivery means detachably coupled to the means for plugging for delivering said means for plugging to a selected location in the lumen, wherein the means for fixing further comprises a segment having a plurality of openings.

7. The lumen occlusion device of claim 6, wherein the openings are evenly spaced.

8. The lumen occlusion device of claim 6 or 7, wherein the openings are round.

* * * * *

UNITED STATES PATENT AND TRADEMARK OFFICE
CERTIFICATE OF CORRECTION

PATENT NO. : 6,599,299 B2
DATED : July 29, 2003
INVENTOR(S) : Leonard S. Schultz It is certified that error appears in the above-identified patent and that said Letters Patent is hereby corrected as shown below:

Column 1,
Line 56, reads "Sep. 14-16, 1992, 10(3):1-20." should be
-- Sep. 14-16, 10(3):1-20. --
Line 65, reads "(¼" – b½")" should be -- (¼" – ½") --

Signed and Sealed this

Eleventh Day of November, 2003

JAMES E. ROGAN
*Director of the United States Patent and Trademark Office*